(12) United States Patent
Lemer

(10) Patent No.: US 7,351,227 B2
(45) Date of Patent: Apr. 1, 2008

(54) DEVICE FOR PROTECTING A SYRINGE, IN PARTICULAR FOR A SYRINGE USED FOR INJECTING RADIOACTIVE PRODUCT (S)

(75) Inventor: Pierre-Marie Lemer, Nantes (FR)

(73) Assignee: Lemer Pax, Carquefou Cedex (FR)

( * ) Notice: Subject to any disclaimer, the term of this patent is extended or adjusted under 35 U.S.C. 154(b) by 454 days.

(21) Appl. No.: 10/363,309

(22) PCT Filed: Sep. 3, 2001

(86) PCT No.: PCT/FR01/02728

§ 371 (c)(1),
(2), (4) Date: Jul. 23, 2003

(87) PCT Pub. No.: WO02/17995

PCT Pub. Date: Mar. 7, 2002

(65) Prior Publication Data

US 2004/0015038 A1    Jan. 22, 2004

(30) Foreign Application Priority Data

Sep. 1, 2000    (FR) .................................. 00 11370

(51) Int. Cl.
*A61M 5/32* (2006.01)
(52) U.S. Cl. ..................................... 604/192
(58) Field of Classification Search ............... 604/187, 604/198, 110, 192, 195, 263, 535, 181, 188, 604/197, 199, 218, 264, 268, 272; 600/5; 588/1, 16, 20; 250/505.1, 506.1, 515.1
See application file for complete search history.

(56) References Cited

U.S. PATENT DOCUMENTS

| | | | | |
|---|---|---|---|---|
| 2,705,494 A | * | 4/1955 | Broadwin | ................ 604/210 |
| 3,807,048 A | * | 4/1974 | Malmin | ................ 433/81 |
| 3,973,554 A | * | 8/1976 | Tipton | ................ 600/5 |
| 4,185,619 A | * | 1/1980 | Reiss | ................ 600/5 |
| 4,615,468 A | | 10/1986 | Gay | |
| 6,159,144 A | * | 12/2000 | Angel et al. | ................ 600/5 |
| 6,162,198 A | * | 12/2000 | Coffey et al. | ................ 604/198 |
| 6,238,374 B1 | * | 5/2001 | Winkler | ................ 604/256 |

FOREIGN PATENT DOCUMENTS

| | | |
|---|---|---|
| BE | 842.989 | 12/1976 |
| EP | 0 661 066 A1 | 7/1995 |
| FR | 2 308 382 | 11/1976 |

* cited by examiner

Primary Examiner—Nicholas D. Lucchesi
Assistant Examiner—Christopher Koharski
(74) Attorney, Agent, or Firm—Young & Thompson

(57) ABSTRACT

A syringe protecting device includes a casing (9) made of a material protecting against radiation, adapted to cover the syringe cylindrical body (3), which casing (9) is associated with a structure (10) likewise made of a material protecting against radiation, designed to form at least a partial protective shield on the rear end of the syringe, while allowing the syringe plunger (4) to be operated. In one particular embodiment, the protective shield is globally shaped like a cylindrical sleeve (10) provided with a base (18); the sleeve (10) is mounted sliding on the protective casing (9) by capping it through its rear end, and it comprises mechanism (20) for being removably secured to the stem (5) operating the syringe plunger (4).

20 Claims, 3 Drawing Sheets

DEVICE FOR PROTECTING A SYRINGE, IN PARTICULAR FOR A SYRINGE USED FOR INJECTING RADIOACTIVE PRODUCT (S)

CROSS-REFERENCES TO RELATED APPLICATIONS

This application is a National Stage of International Application No. PCT/FR01/02728 filed on Sep. 3, 2001 under 35 U.S.C. § 371, which claims priority to French Application No. 00 11370 filed Sep. 1, 2000.

BACKGROUND OF THE INVENTION

This invention concerns the devices of the <<syringe protector>> type fitting the syringes of conventional type used notably for the injection of radioactive product(s) to ensure the protection of operators against exposure to high energy beams (for example the beams emitted by iodine 131, fluorine 18, oxygen 15 or carbon 11).

DESCRIPTION OF THE RELATED ART

The protection devices of such kind currently available on the market consist of an envelope substantially cylindrical in shape, of radioprotective material (lead; tungsten . . . ) suited to cover the cylindrical body of the syringe. This protective envelope comprises an orifice at its front end which enables the passage of the injection needle or of the reception cone of this needle; it also comprises an orifice at its rear end, which is used for the insertion and the withdrawal of the syringe body, as well as for operating the stem of the syringe piston.

These structures fulfill relatively well their protective role but there remains a risk of irradiation through the end orifices of the protective envelope. In particular, the operator of the syringe is exposed directly to this risk of irradiation through the rear end of this syringe, on the piston side.

SUMMARY OF THE INVENTION

This invention concerns therefore a solution to reinforce the protection provided by this kind of structure.

The protection device for syringe, according to this invention, comprises an envelope of radioprotective material, suited to cover the cylindrical syringe body, which envelope is associated with a structure also made of radioprotective material, which is laid out to form a protective shield at least partially at the rear end of the syringe body while enabling the operation of the piston of said syringe.

Still according to the invention, the protective envelope comprises an opening at its front end to let through the needle of the syringe or the reception cone of this needle, and an opening at its rear end for the insertion and the withdrawal of said syringe, as well as for operating the stem relative to its piston; moreover, there is provided an added-on structure of radioprotective material, which is laid out to form a protective shield at least partially opposite the opening arranged at the rear end of the protective envelope, while enabling the operation of the piston of the syringe.

According to a first embodiment, the protective shield has the general shape of a tubular jacket fitted with a bottom; this jacket covers the protective envelope at the rear end thereof and it comprises removable interconnection means with the stem which operates the piston of the syringe.

Preferably, the tubular jacket of radioprotective material is mounted to slide over the protective envelope. On the other hand, the cylindrical body of the tubular jacket has advantageously a length which is suited to cover the rear end of the protective envelope regardless of the extraction level of the stem which operates the syringe piston.

According to another feature, the removable interconnection means of the tubular jacket with the stem which operates the syringe piston consist of a lock laid out to press the head of said operating stem against the internal face of the bottom of said jacket.

According to another aspect, the protection device comprises means which enable to lock the tubular jacket on the protective envelope in order to block the position of the piston of the syringe; these particular means consist advantageously of two knurled knobs diametrically opposed.

Preferably, these knurled knobs are integral with the protective envelope and they co-operate with longitudinal openings provided in the tubular jacket, which openings emerge at the front end of this jacket.

According still to another aspect, the protection device according to this invention comprises removable interconnection means of the syringe body with the protective envelope. These means consist advantageously of a lock suited to press the end collar of the syringe body against the rear end of the protective envelope; the operating member of this lock protrudes across a longitudinal opening arranged in the tubular jacket, which opening emerges at the front end of said jacket.

According to another embodiment, the protective shield consists of two additional retractable half-parts laid out to be placed at the rear end of the protective envelope 27, and whereof the junction edges are shaped to match the contour of the stem which operates the piston of the syringe.

Both additional half-parts can be mounted to slide on a guiding cradle positioned around the rear end of the protective envelope. This cradle holds both half-parts at the rear end of the protective envelope; it enables to bring both half-parts closer together in order to blank off the opening of the rear end of this protective envelope around the operating stem of the syringe piston, and it enables said half-parts to retract in order to position the syringe in the protective envelope, as well as its withdrawal.

Preferably, both additional half-parts are fitted with reverse shoulders on their junction edges, making up partial covering means. They also comprise advantageously extensions forming a covering skirt for the rear end of the protective envelope.

BRIEF DESCRIPTION OF THE DRAWINGS

But the invention will be better illustrated, without being limited thereto, by the following description of various particular embodiments, given solely for exemplification purposes and represented on the appended drawings wherein.

DESCRIPTION OF THE PREFERRED EMBODIMENTS

Figure 1:
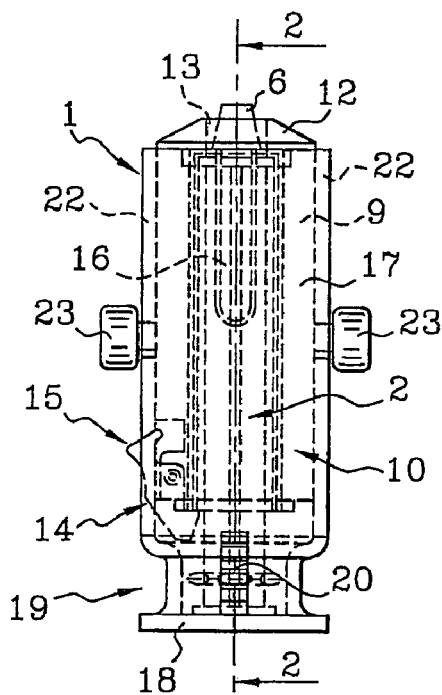
FIG. 1 is a lateral view of a first possible embodiment of a syringe protection device according to this invention, the protected syringe being here represented with its piston stem integrally <<retracted>>.

FIGS. 1 to 4 illustrate a first embodiment of a device 1 enveloping a syringe 2 to protect the operators against the radiation emitted by the radioactive product(s) intended to be injected.

The syringe 2 is of conventional type, made of a cylindrical syringe body 3 associated with an internal piston 4 which is operated by a stem 5 with a cross-like section. The syringe body 3 is extended by a truncated cone 6 at its front end, intended to receive the injection needle, not represented; its rear end comprises a peripheral collar 7.

On the other hand, the external end of the stem 5 which operates the piston 4 is fitted with a flat head 8.

The syringe protection device 1 consists mainly of a cylindrical envelope 9 which surrounds the syringe body 3, and of a sliding jacket 10 which constitutes a protection shield by the rear end of said envelope 9.

The cylindrical envelope 9 is made of radioprotective material, such as tungsten for example. It is lined internally by a sheath 11 of plastic material whereof the internal diameter corresponds, including the clearance, to the external diameter of the syringe body 3. This sheath 11 facilitates the positioning and the withdrawal of the syringe body 3 within the envelope 9; according to the material used, it may also play a part in the radioprotection function.

The front end of the protective envelope 9 is fitted with an added-on truncated cowling 12, also made of tungsten, fitted with a central orifice 13 letting through the truncated cone 6 of the syringe. This orifice 13 is reduced in size to limit the beam leakage; the cowling 12 also constitutes an end stop for the syringe body 3.

At the rear end of the cylindrical envelope 9, one can note the presence of a quick fastening/releasing means 14 which enables to maintain the syringe body 3 inside said envelope 9. This fastening/releasing means 14 consists of a removable lock which presses the end crown 7 of the syringe body 3 against the rear end of the envelope 9; this lock is here in the form of a squeezer dog operated manually by means of a protruding extension 15, and subject to a recall spring.

As regards the front end of the cylindrical envelope 9, one can note the presence of a lead glass sight-window 16 which enables to access visually the useful portion of the graduations of the syringe body 3.

The jacket 10 which is associated with the protective envelope 9 is also made of radioprotective material, such as tungsten for example. This jacket 10 has the general shape of a cylindrical tube 17 whereof the internal diameter corresponds, including the clearance, to the external diameter of the envelope 9, and whereof one of the ends is blanked off by a bottom element 18. Just before the bottom element 18 one can note the presence of an annular hollow 19 arranged in the tubular section 17.

At the internal face of the bottom element 18, a removable lock 20 in the form of a squeezer dog is arranged to fasten the stem 5 which operates the syringe piston 4. This lock 20 has a structure similar to that of the locking member 14 described previously; it is accessible through an opening 21 arranged in the tubular section 17, at the annular hollow 19.

Figure 3:
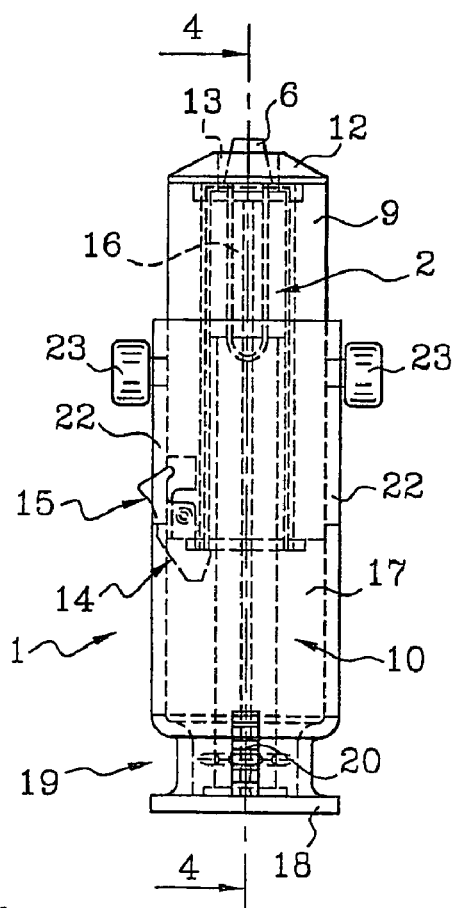
FIG. 3 shows the same protection device with the stem of the piston of the syringe partially extracted.

Over a portion of the length of the tubular element 17 there have been provided two longitudinal openings 22 diametrically opposed visible on FIGS. 1 and 3. Both these openings 22 emerge at the front end of the tubular element 17; they are intended to co-operate with knurled knobs 23 integral with the cylindrical envelope 9 in order to lock the tubular jacket 10 on said envelope 9. One of both longitudinal openings 22 is also used to let through the extension 15 of the squeezer dog 14.

The jacket 10 is placed on the cylindrical envelope 9 by the rear end thereof, once the syringe 2 has been inserted into its receiving structure 9, 11. The cylindrical tube 17 is guided on the envelope 9 until its flat head 8 of the operating stem 5 is interconnected automatically with the bottom element 18 of the jacket, under the action of the lock 20.

In this position, the jacket 10 forms a shield which protects the operator from the radiation emitted in the axis of the syringe through the rear opening of the protective envelope 9.

The syringe 2 is then ready to be used, whereas the operation of its piston 4 also consists in making the jacket 10 slide over the envelope 9. This sliding is possible when the knurled knobs 23 are loose; these knurled knobs 23 as well as the annular recess 19 may then be used as resting points for the fingers, when filling the syringe or when injecting the product.

The knurled knobs 23 are tight when one wishes to lock the position of the jacket 10 on the protective envelope 9; this locking enables to block the position of the piston 4 in the syringe body 3 and one thus avoids any accidental flow of the radioactive product through the injection needle.

The tubular section 17 of the jacket 10 has a length which is suited to cover the rear end of the protective envelope 9 regardless of the extraction level of the stem 5. According to this extraction level, this tubular section 17 doubles more or less the cylindrical envelope 9 and it reinforces therefore the protection conferred by said envelope.

Figure 2:
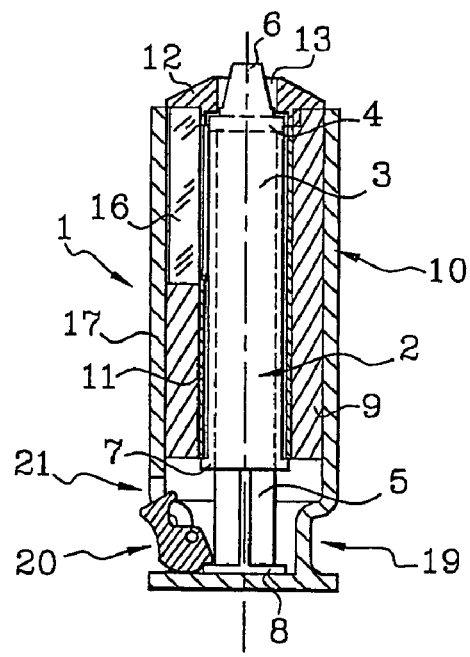
FIG. 2 is a sectional view along 2-2 of FIG. 1.
Figure 4:
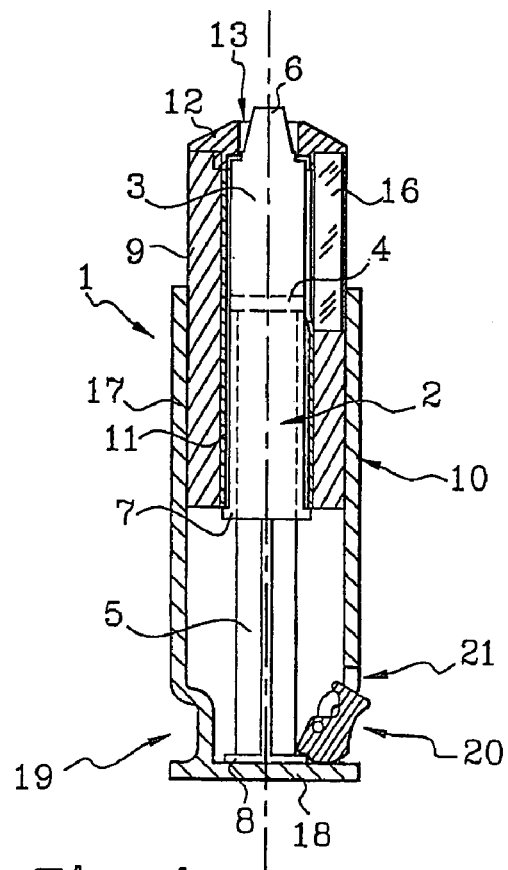
FIG. 4 is a sectional view along 4-4 of FIG. 3.

As represented on FIGS. 1 and 2, the length of the tubular section 17 is suited to cover completely the envelope 9 when the piston 4 of the syringe is integrally retracted. FIGS. 3 and 4 show the syringe with the stem 5 which operates the piston 4 partially extracted.

When the injection of the radioactive product is complete, the syringe is extracted from its protective device by operating both squeezer dogs 14 and 20.

Figure 5:
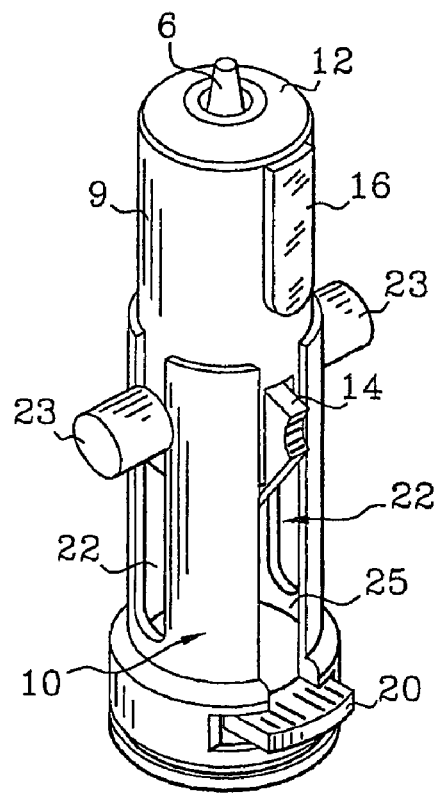
FIG. 5 is a perspective view of an embodiment variation of the syringe protection device illustrated on FIGS. 1 to 4.
Figure 6:
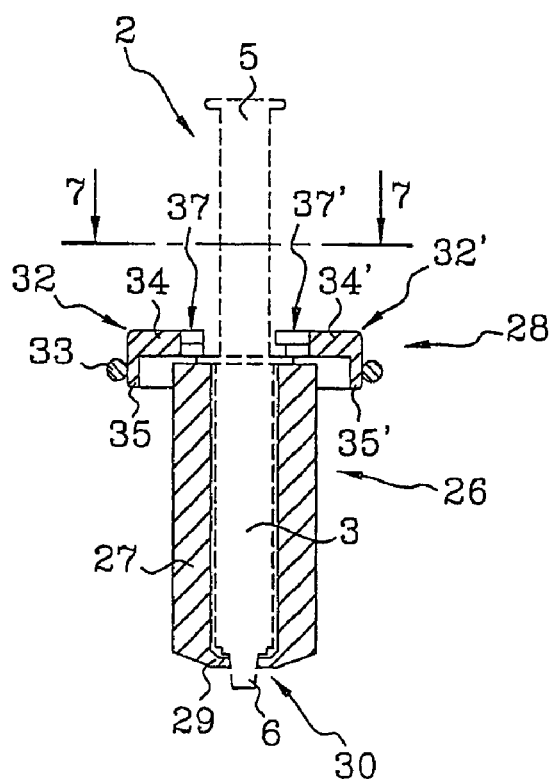
FIG. 6 is a longitudinal sectional view of another possible embodiment of a syringe protection device according to this invention, with a protective shield, here in <<open>> position, composed of two additional half-parts.
Figure 7:
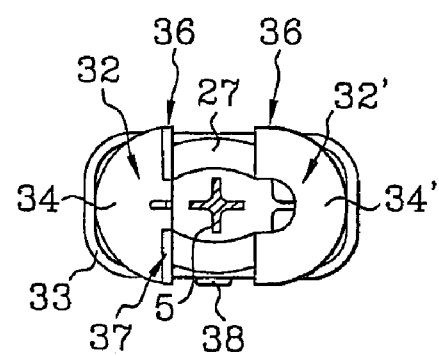
FIG. 7 is a sectional view along 7-7 of FIG. 6.

FIG. 5 represents a variation of the embodiment of the syringe protection device illustrated on FIGS. 1 to 4.

Here, the protective envelope 9 is the same with its armoured sight-window 16 and with its cowling 12 through the central orifice of which passes the end truncated cone 6 of the syringe. There is also the tubular jacket 10 with its emerging longitudinal grooves 22 which co-operate with the knurled knobs 23 integral with the envelope 9.

In this variation of the embodiment, the rear end section of the jacket 10 has been modified slightly; it does not comprise any annular hollows and the removable lock 20 corresponds to a model different of that illustrated on FIGS. 1 to 4.

On the other hand, the lock 14 which ensures removable interconnection between the syringe body and the protective envelope 9 extends through a longitudinal groove 25 which is dedicated thereto, independent of both grooves 22 used for letting through the feet of the knurled knobs 23.

FIGS. 6 to 12 illustrate another possible embodiment of a syringe protection device according to this invention.

In the following description, one has kept the previous references allocated to the injection syringe for simplification purposes.

This syringe protection device 26 consists of a cylindrical envelope 27 of radioprotective material such as tungsten, associated with an added-on shield 28, also made of radioprotective material such as tungsten, enabling removing blanking off of the rear opening of said envelope 27.

The cylindrical envelope 27 receives the syringe body 3; its front end comprises an inner annular return 29 which only leaves a small central orifice 30 just sufficient for letting through the end truncated cone 6 of the syringe.

The added-on shield 28 consists of two additional half-parts 32 and 32', here in the form of half-shells, which are suited to be positioned on the rear end of the cylindrical envelope 27. Both these half-shells 32 and 32' are mounted to slide on a supporting cradle 33 which, while ensuring their interconnection, enables to bring them closer to or further from a plane perpendicular to the axis of the protective envelope 27. Both rectilinear parallel portions of the cradle 36, which constitute the guiding portions of both half-shells 32 and 32', are slightly tight against the cylindrical envelope 27 to maintain the shield 28 in position. To secure this hold, one may also contemplate to embed the central section of these rectilinear portions in throats formed on the periphery of the protective envelope 9.

Figure 8:
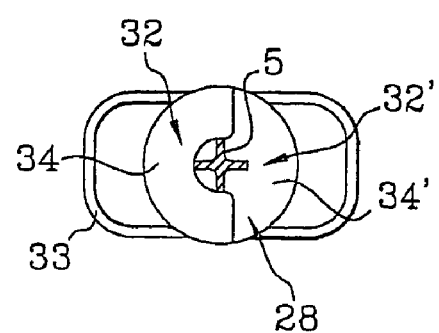
FIG. 8 is a view similar to FIG. 7, the protective shield being here represented in <<closed>> position.
Figure 9:
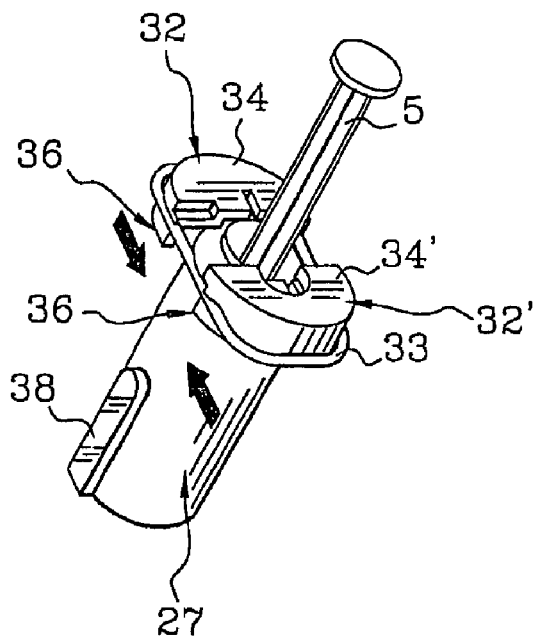
FIGS. 9 and 10 are perspective views, respectively ¾ rear and ¾ front views which show the protection device of FIGS. 6 to 8 with the protective shield in <<open>> position.
Figure 10:
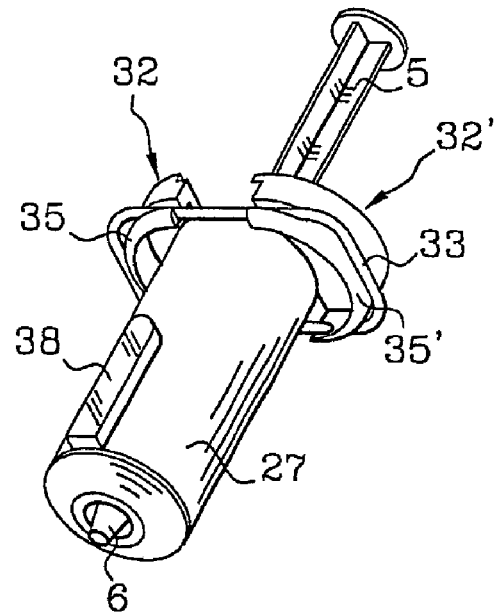
Figure 11:
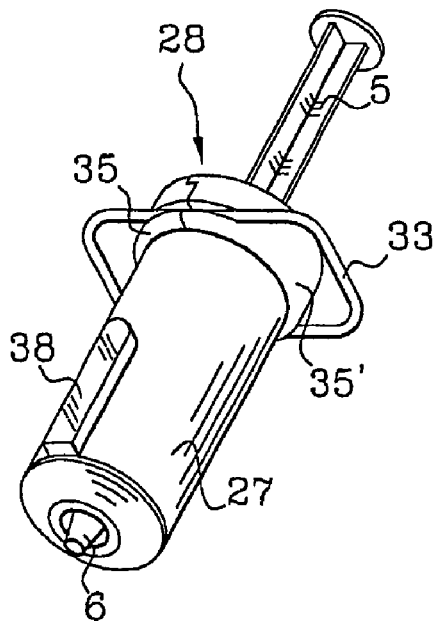
FIGS. 11 and 12 are perspective views, respectively of ¾ front and ¾ rear views which show the same protection device with the protective shield in <<closed>> position.
Figure 12:
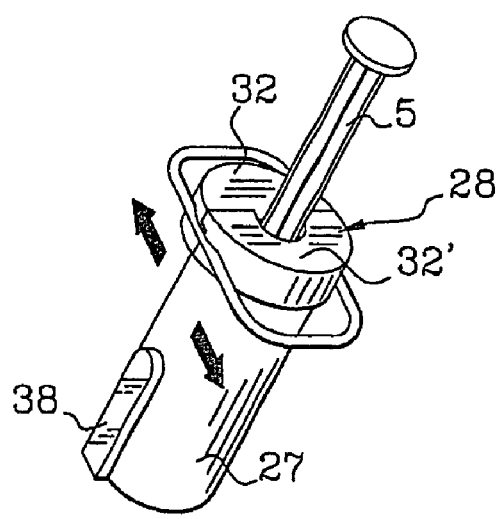

When both half-shells 32 and 32' are spaced from one another, the syringe body 3 can be inserted in the protective envelope 27 (FIGS. 6, 7, 9 and 10); once the syringe is in position, both these half-shells are brought closer manually to blank off the rear orifice of said envelope 27 while hugging the stem 5 which operates the piston of the syringe (FIGS. 8, 11 and 12).

Both half-shells 32 and 32' consist of a blanking off element 34, 34' semicircular in shape, extended by a semicylindrical skirt section 35, 35'. These skirt sections 35, 35' will hug the rear end of the envelope 27 when both half-shells 32 and 32' are placed in radioprotection active position; they comprise lateral grooves 36 which guide half-shells 32, 32' over the parallel rectilinear lengths of the cradle 33.

The junction edges of both blanking off elements 34 and 34' are formed to hug as much as possible the contour of the stem 5 with a cross-like section, when they are brought closer to one another. Solely the surface corresponding to the cross-like section of this stem 5 is not protected, which limits the risks of beam leakage. On the other hand part, these junction edges also comprise reverse shoulders, 37, 37' which ensure partial covering of both blanking off elements 37, 37' when they are juxtaposed, which enables to secure the radioprotection.

Once both half-shells 32, 32' have been brought closer to one another, the stem 5 of the syringe can be operated conventionally by sliding through the protective shield 28.

FIGS. 7 and 9 to 12 underline the presence of an armoured sight-window 38, made of lead glass, fitting the front end of the cylindrical envelope 27 to access visually the graduations of the syringe body 3.

Still according to another possible embodiment the cylindrical envelope which surrounds the syringe body 3 can be associated with a pellet, for example circular, made of radioprotective material, removably fixed on the flat head 8 of the syringe piston 4.

The invention claimed is:

1. A protection device for a syringe used for injection of radioactive product(s), comprising:
    an envelope of radioprotective material, the envelope shaped to cover a cylindrical body of a syringe, the syringe further including a needle, a reception cone, a piston, the piston including a stem with a head,
    an opening fitted at a front end of the envelope, the opening for letting through the needle or the reception cone, and
    another opening at a rear end of the envelope for insertion and withdrawal of the syringe, as well as for operating the stem, and
    a structure of radioprotective material associated with the envelope, the structure forming a protective shield at least partially facing the another opening at the rear end of the envelope, while enabling the operation of the piston, wherein,
    the protective shield has the general form of a tubular jacket fitted with a bottom,
    said jacket covers the another opening at the rear end of the protective envelope,
    said jacket comprises interconnection means removable with respect to the stem, and
    the removable interconnection means comprises a lock arranged to press the head of the operating stem against an internal face of the bottom of said jacket.

2. A protection device for a syringe used for injection of radioactive product(s), comprising:
    an envelope of radioprotective material, the envelope shaped to cover a cylindrical body of the syringe, the syringe further including a needle, a reception cone, a piston, a body with an end collar, the piston including a stem with a head,
    an opening fitted at a front end of the envelope, the opening for letting through the needle or the reception cone, and another opening at a rear end of the envelope for insertion and withdrawal of the syringe, as well as for operating of the stem, and
    a structure of radioprotective material associated with the envelope, the structure forming a protective shield at least partially facing the another opening at the rear end of the envelope, while enabling the operation of the piston,
    wherein the protective shield is fitted with a bottom and covers the another opening at the rear end of the protective envelope, and the protective shield comprises removable interconnection means with the stem which operates the piston, the removable interconnection means comprising a lock arranged to press the head of the operating stem against the internal face of the bottom of said protective shield.

3. A device according to claim 2, wherein the protective shield is mounted to slide over the protective envelope.

4. A device according to claim 2, wherein the protective shield is tubular and mounted to slide over the protective envelope.

5. A device according to claim 2, wherein the protective shield is a jacket and mounted to slide over the protective envelope.

6. A device according to claim 2, wherein the protective shield comprises two half-parts and mounted to slide over the protective envelope.

7. A device according to claim 2, wherein the protective shield is a tubular jacket mounted to slide over the protective envelope.

8. A device according to claim 7, wherein a cylindrical body of the tubular jacket has a length which is suited to cover the rear end of the protective envelope regardless of the extraction level of the stem.

9. A device according to claim 7, further comprising knurled knobs integral with the protective envelope which co-operate with longitudinal openings arranged in the tubular jacket, wherein the openings emerge at the front end of said jacket.

10. A device according to claim 9, removable interconnection means of the syringe body with the protective envelope, which interconnection means consist of a lock suited to press the end collar of the syringe body against the rear end of said protective envelope, whereas the operating member of said lock protrudes across one of the longitudinal openings arranged in the tubular jacket, wherein the one longitudinal opening emerges at the front end of said jacket.

11. A device according to claim 7, further comprising means which enable the positioning of the tubular jacket to the protective envelope.

12. A device according to claim 2, further comprising means which enable the positioning of the protective shield to the protective envelope.

13. A device according to claim 2, further comprising means to lock the protective shield to the protective envelope comprising two knurled knobs diametrically opposed.

14. A device according to claim 2, wherein the protective shield comprises two retractable half-parts laid out to be positioned on the another opening at the rear end of the protective envelope and whereof junction edges are formed to match a contour of the stem.

15. A device according to claim 14, characterised in that both of the two half-parts comprise extensions which form a covering skirt of the rear end of the protective envelope.

16. A device according to claim 2, wherein the protective shield comprises two half-parts mounted to slide in a guiding cradle positioned around the two half-parts and around the rear end of the protective envelope.

17. A device according to claim 2, wherein the protective shield comprises two half-parts fitted with reverse shoulders on their junction edges, forming partial covering means.

18. A device according to claim 2, wherein the protective shield has the form of a pellet made of radio-protective material, and removably fixed on the head of the syringe piston.

19. A device according to claim 2, further comprising means which enable the positioning of the protective shield to the protective envelope.

20. A device according to claim 2, wherein the protective shield comprises two half-parts fitted with reverse shoulders on their junction edges, forming partial covering means.

* * * * *